United States Patent [19]

Shuminov

[11] Patent Number: 5,808,554
[45] Date of Patent: Sep. 15, 1998

[54] MOISTURE DETECTING LINER FOR A DIAPER AND A PROCESS FOR MANUFACTURE THEREOF

[76] Inventor: Asher Shuminov, P.O.B. 480, 20100 Carmiel, Israel

[21] Appl. No.: 860,688
[22] PCT Filed: Dec. 28, 1995
[86] PCT No.: PCT/US95/17087
   § 371 Date: Jul. 2, 1997
   § 102(e) Date: Jul. 2, 1997
[87] PCT Pub. No.: WO96/20681
   PCT Pub. Date: Jul. 11, 1996

[30] Foreign Application Priority Data

Jan. 3, 1995 [IL] Israel .......................................... 112226

[51] Int. Cl.⁶ .................................................. G08B 21/00
[52] U.S. Cl. ............................................ 340/604; 604/361
[58] Field of Search .................................... 340/604, 603, 340/605, 573; 604/361; 200/61.04

[56] References Cited

U.S. PATENT DOCUMENTS

| | | |
|---|---|---|
| 5,036,859 | 8/1991 | Brown . |
| 5,266,928 | 11/1993 | Johnson . |
| 5,291,181 | 3/1994 | DePonte . |
| 5,392,032 | 2/1995 | Kline et al. . |
| 5,557,263 | 9/1996 | Fisher et al. ............................ 340/604 |
| 5,568,128 | 10/1996 | Nair ........................................ 340/604 |

Primary Examiner—Jeffery A. Hofsass
Assistant Examiner—Sihong Huang
Attorney, Agent, or Firm—Browdy and Neimark

[57] ABSTRACT

A diaper liner comprising an electrically insulating sheet material having disposed thereon first, second and third separated electrically conductive tracks which become short-circuited when the liner is exposed to moisture, at least one end of each of the electrically conductive tracks being in the form of a conductive pad printed on the liner for permitting easy connection thereto of a moisture alarm circuit. The third conductive track is commonly connected so that the first and the third tracks are short-circuited by urine whilst the second and third tracks are short-circuited by feces.

13 Claims, 5 Drawing Sheets

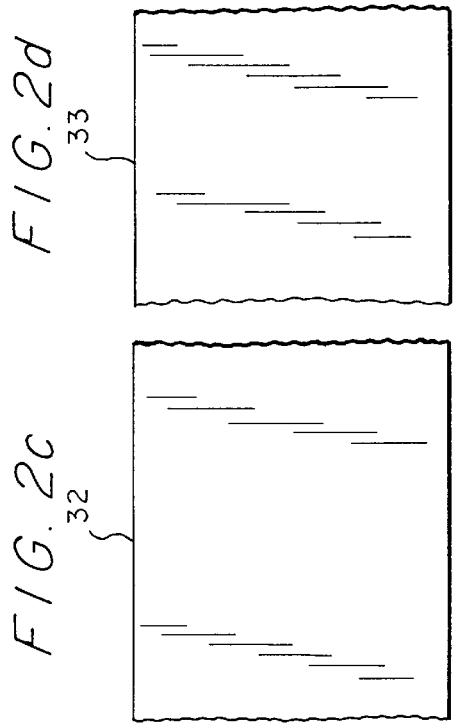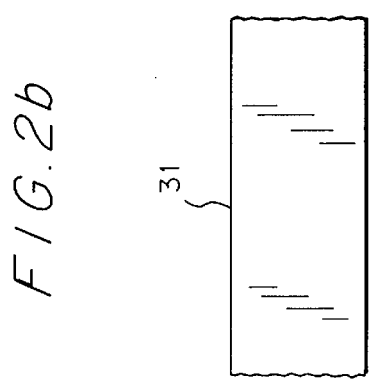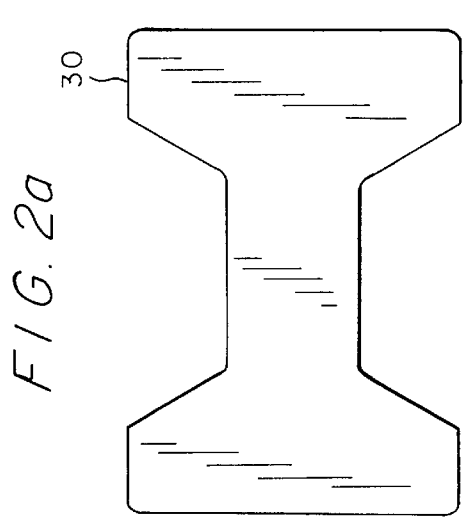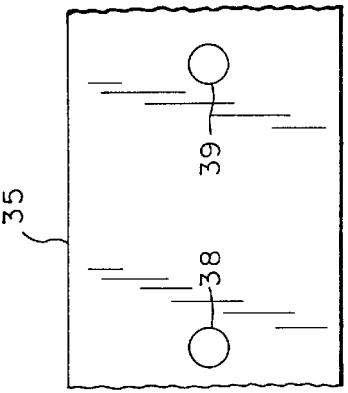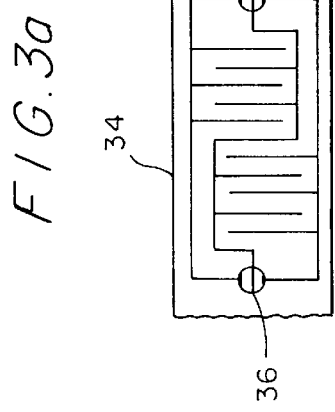

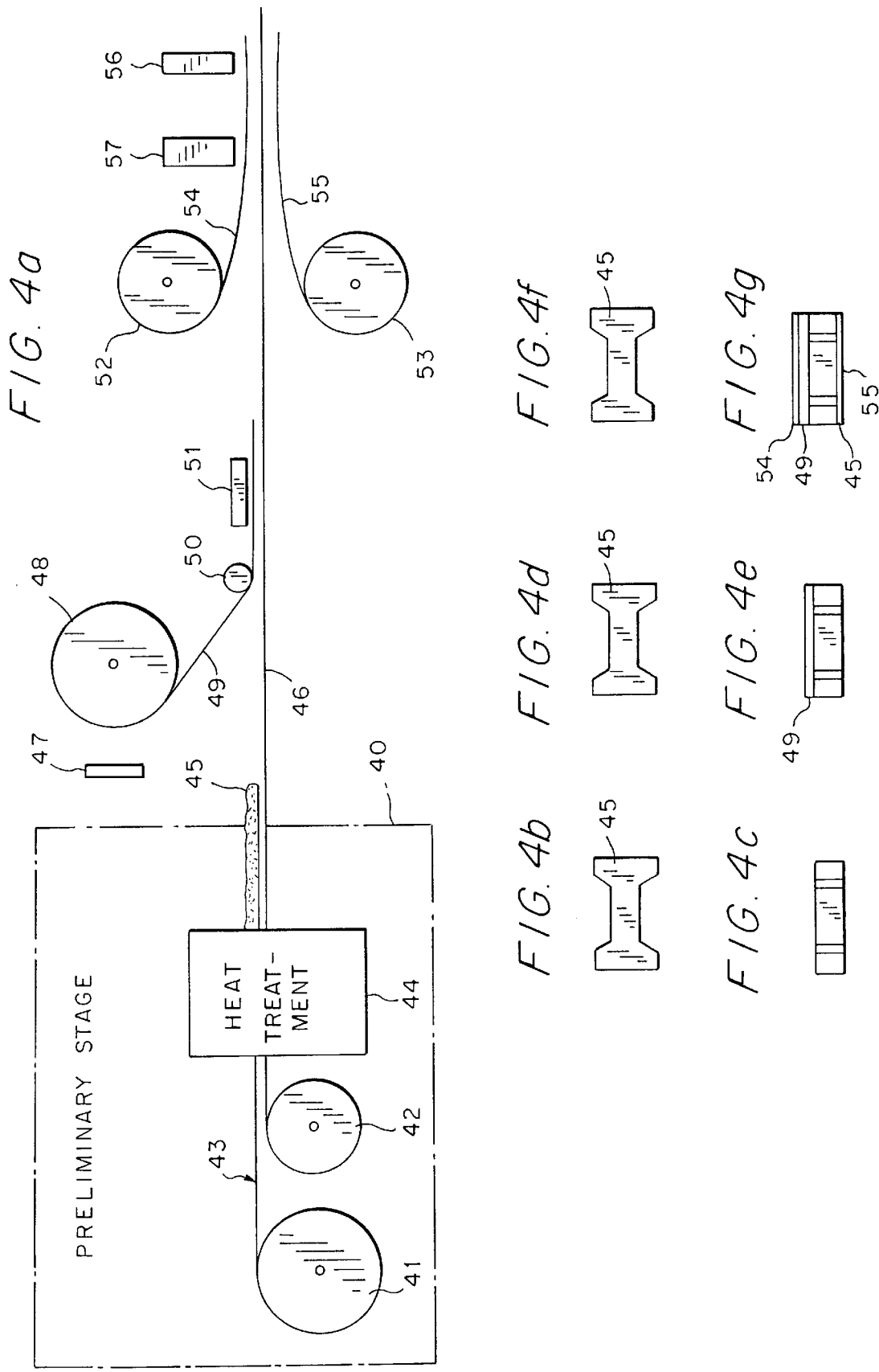

MOISTURE DETECTING LINER FOR A DIAPER AND A PROCESS FOR MANUFACTURE THEREOF

FIELD OF THE INVENTION

This invention relates to moisture sensing pads for sensing moisture and, in particular, to use of such pads in conjunction with disposable diapers and to the manufacture of such diapers.

BACKGROUND OF THE INVENTION

The requirement to detect wetness in the groin area of a child or an incontinent adult has long been recognized and is well addressed in the prior art. Common to nearly all prior art approaches is the placement of a pair of spaced apart electrodes, typically positioned in a diaper within a region thereof subject to wetness and having a connection means for releasably connecting thereto a moisture alarm circuit. When the diaper becomes wet, the moisture short-circuits (the electrodes) thereby completing the moisture alarm circuit which produces a visible or audible alarm.

Since disposing stiff wire electrodes near the groin area is hardly comfortable for the wearer, disposable pads having flexible strip electrodes attached to a surface thereof have been proposed: the flexible strip electrode typically being in the form of a conductive liquid which is painted, or otherwise disposed, on the pad and then allowed to dry.

In all prior art diaper wetness detectors, some sort of clasp is attached to the moisture pad, by rivetting example, so as to enable connection thereto and disconnection therefrom of a moisture alarm circuit. The clasps are themselves connected to respective ends of the two electrodes so that, when the moisture alarm circuit is connected to the clasps, the desired electrical connection to the electrodes is effected. However, the clasps are relatively expensive to manufacture and assemble and the required connection of the external moisture alarm circuit can be an awkward operation.

Yet a further problem which has been addressed by the prior art relates to the disposition of the electrodes within the diaper in such a form that, regardless of which part of the moisture pad becomes wet, the electrodes will always be short-circuited. To this end, it is known to provide the electrodes in the form of a matrix disposed over a large area of the moisture pad which, when in use, is located within the groin area of the user.

The prior art also addresses the need to provide an alarm signal without disturbing the user. This is particularly relevant when disposable diapers are used for incontinent adults, especially hospital patients, since whilst it is obviously important for the nursing staff to monitor a patient's urination, it is also desirable to do so in a manner which does not embarrass the patient. To this end, there has been proposed a remote moisture alarm detector comprising a transmitter coupled to the moisture pad and a remote receiver for receiving a signal transmitted thereby and being coupled to an indicator means for producing an audible or visible signal. By such means, the alarm signal may be monitored remotely by the nursing staff, whilst assuring discretion for the patient.

All of the features summarized above are well described in U.S. Pat. No. 5,036,859 (Brown), the disclosure of which is incorporated herein by reference.

Brown discloses an apparatus which detects urination by a user including a urine sensing pad for placement over the pubic and/or perianal areas of a user. The sensing pad includes a pair of electrodes on a backing sheet, and an absorbent cover sheet which is glued or heat/sealed to the backing sheet. An indicator box is adapted for coupling to the electrodes so as to produce either a local or remote alarm when urine moistens the pad and short-circuits the electrodes.

The utility of all prior art approaches is based on the underlying assumption that, at the very onset of urination, the diaper must be changed. This, of course, is good news for the manufacturer of diapers but, as any experienced parent will confirm, is unnecessary in practice. Diapers are made to be absorbent and, whilst certainly a diaper must not be allowed to become saturated with urine, it would be overreacting to change the diaper at the very onset of urination when the moisture alarm circuit is triggered. Whilst this is certainly true so far as urination is concerned, it is categorically not so where fecal excrement is concerned since experience shows, and medical research confirms, that tardy changing of a soiled diaper will result in diaper rash and severe discomfort for the user. It is, of course, true that fecal expulsion is almost invariably accompanied by urination which would activate the alarm connected to prior art moisture sensing pads.

However, there is no way for the parent or nursing staff to discriminate between that urination which is unaccompanied by fecal excrement, on the one hand, and that urination which is accompanied by fecal excrement, on the other hand. As a result, there is no choice but to perform a manual (or nasal!) investigation in order to establish whether a soiled diaper must be changed without delay, since it is virtually impossible to open a disposable diaper without destroying the adhesive properties of the diaper's fixing tabs. In other words, once it is determined that the alarm signal was given as a result of the onset of urination only, there remains no option, once the diaper has been opened, but to replace it.

It would, therefore, clearly be useful if some means were provided for discriminating between fecal excrement and urine in a diaper.

In those prior art references, such as U.S. Pat. No. 5,036,859, described above, which relates to the provision of a moisture detector pad, the pad itself is usually formed of an absorbent material which is consequently bulky. Such a pad is disposed between the diaper and the groin area of the user and thus significantly adds to the bulk in that area. Furthermore, the moisture pad is supplied as an ancillary device and must therefore be rendered sufficiently sturdy so as to permit connection thereto of the external moisture alarm circuit. All of these factors contribute to the expense of the moisture pad so that it becomes a not insignificant fraction of the cost of the diaper itself. Clearly, the cost of the moisture pad would be significantly lowered if the moisture pad were reduced to its bare essentials: namely a thin liner material having an electrically conductive matrix thereon with connection pads for connecting thereto an external moisture alarm circuit. If such a conductive liner were amenable to mass production and were provided as an integral part of the diaper, during manufacture thereof, then the resulting diaper would have no increased bulk and the additional expense, compared with the cost of the diaper itself, would be trivial. However, such a requirement is not addressed by the prior art.

SUMMARY OF THE INVENTION

It is an object of the invention to provide a liner for a diaper which overcomes the drawbacks associated with hitherto proposed moisture detector pads.

It is a further object of the invention to provide such a liner having two separate areas of electrically conductive matrices for detecting moisture or soiling in respective regions of a user.

It is also an object of the invention to integrate such a liner within a disposable diaper during manufacture and to modify a diaper production line accordingly.

These objects are realized in accordance with one aspect of the invention by a liner for a diaper, said liner comprising:

an electrically insulating sheet material having disposed thereon first and second separated electrically conductive tracks which become short-circuited when the liner is exposed to moisture, at least one end of each of the electrically conductive tracks being in the form of a conductive pad printed on the liner for permitting easy connection thereto of a moisture alarm circuit.

It is to be understood that in the context of the invention, the term "printed" has any of its usual dictionary meanings: namely, pressing or stamping or drawing, tracing or otherwise marking on a surface, or to deliver information via a computer such as, for example, by means of a plotting device and the like. All that is important, in this respect, is that by printing the conductive tracks on to the liner using any one of these processes, the conductive liner is amenable to mass production techniques and is therefore so inexpensive that its inclusion within a diaper as an integral component thereof during manufacture, adds little cost to the resulting diaper.

According to another aspect of the invention, there is provided a process for manufacturing a diaper having an integral moisture detecting liner, said process including the steps of:

(a) pre-printing a liner with an electrically conductive matrix comprising at least two electrically conductive tracks terminated with a connection pad at at least one end, (b) locating said liner in an assembly line at a location downstream of a preliminary stage from which a pre-cut absorbent layer emerges, (c) conveying the pre-cut absorbent layer towards said liner, (d) producing an integral absorbent layer/liner combination by disposing the liner on the absorbent layer so that an end of the liner is in substantial alignment with an end of the absorbent layer, (e) rotating respective first and second rolls of innermost and outermost layer material downstream of the liner location so as to apply the innermost and outermost layers on opposite sides of the absorbent layer/liner combination, and (f) forming an external connection to said connection pad, so as to allow connection thereto of a moisture alarm circuit.

In such a process the liner may be in the form of separate sheets of pre-cut material arranged for aligning with the absorbent layer during manufacture of the diaper. Preferably, however, the liners are formed by pre-printing a roll of liner material with a plurality of equally-spaced electrically conductive matrices each comprising at least two electrically conductive tracks terminated with a connection pad at at least one end. Such a roll may be integrated into existing diaper production lines, so as to allow for synchronization of the roll with the production process.

Either process allows for mass manufacture of diapers using existing assembly lines whilst integrating therein an electrically conductive liner at almost negligible cost to the manufacturer.

BRIEF DESCRIPTION OF THE DRAWINGS

For a clearer understanding of the invention and to appreciate how the same may be carried out in practice, some preferred embodiments will now be described, by way of non-limiting example only, with reference to the accompanying drawings in which:

FIGS. 2a to 2d show schematically component layers associated with a conventional disposable diaper;

FIGS. 3a and 3b show modifications relating to the diaper layers shown in FIGS. 2b and 2c which must be effected so as to produce a diaper having integral therewith a liner according to the invention;

FIG. 4a shows schematically a production line for manufacturing the diaper shown schematically in FIGS. 3a and 3b;

FIGS. 4b to 4g show respective plan and side elevations of the diaper components at various stages of production;

DETAILED DESCRIPTION OF PREFERRED EMBODIMENTS

Figure 1:
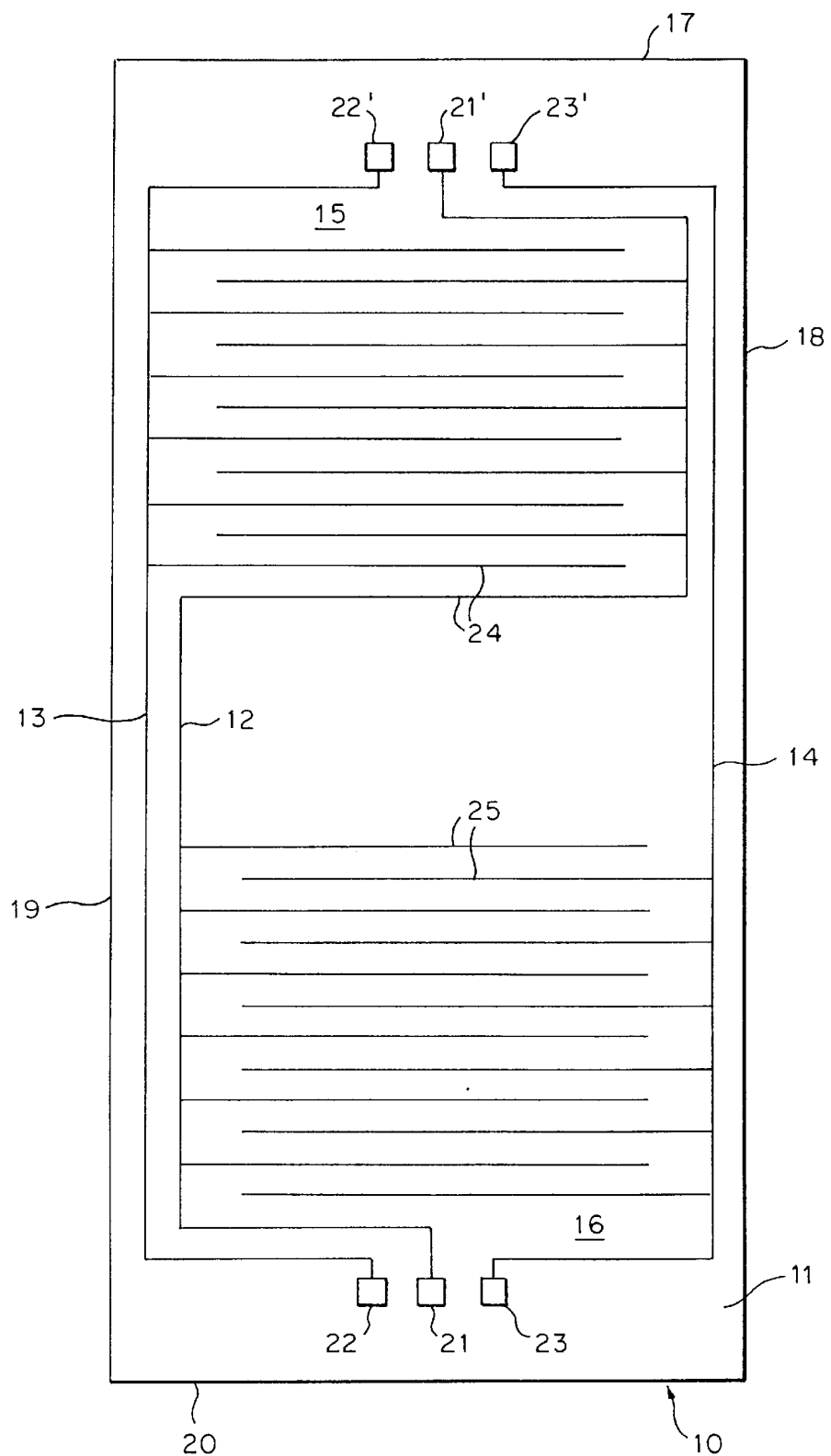
FIG. 1 is a schematic representation of a liner according to the invention having an electrode matrix printed thereon.

FIG. 1 is a schematic representation of a liner depicted generally as 10 and comprising an insulating backing sheet 11 on which there is printed an electrical circuit comprising first, second and third electrically conductive tracks or rails 12, 13 and 14, respectively. The first electrically conductive track 12 forms a common rail extending across upper and lower portions of the liner 10 and represented by reference numerals 15 and 16, respectively. As a result of such a configuration, the first and second tracks 12 and 13 become short-circuited when the upper portion 15 of the liner 10 becomes moist; whilst the first and third tracks 12 and 14 are short-circuited when the lower portion 16 of the liner 10 becomes moist. Since the first track 12 is common to both the upper portion 15 and the lower portion 16 of the liner 10, it constitutes a common rail extending across both portions of the liner.

Specifically, the first rail 12 is in the form of a generally S-shaped rail extending longitudinally from a first end 17 of the liner 10 partially along a first side 18 thereof and continuing partially along a second side 19 of the liner towards a second end 20 thereof. The second rail 13 extends longitudinally from the first end 17 of the liner along the second side 19 thereof towards the second end 20. The third rail 14 extends longitudinally from the second end 20 of the liner at least partially along the first side 18 thereof. Each of the three rails 12, 13 and 14 is terminated in a connection pad 21, 22 and 23 respectively at the second end 20 of the liner so as to permit external connection of a moisture alarm circuit thereto as will be described in more detail below.

In order that such moisture alarm circuit can be connected to either the front or rear of a diaper, it is preferable that all three rails 12, 13 and 14 extend between both ends of the liner and are terminated at the first end 17 also with corresponding connection pads 21', 22' and 23'.

Interconnecting the first and second rails 12 and 13 in the upper portion 15 is a set of equipotential bars 24, whilst a similar set of equipotential bars 25 interconnects the first and third rails 12 and 14 in the lower portion 16. Each set of equipotential bars 24 and 25 extends laterally between the corresponding rails so as to form respective maze-shaped matrices in the upper and lower portions 15 and 16 of the liner 11.

FIGS. 2a, 2b, 2c and 2d show, respectively components in a conventional disposable diaper. FIG. 2a shows an I-shaped absorbent layer 30 formed of a cotton-wool cellulose-type material. FIG. 2b shows a second layer 31 being an internal liner formed of tissue-type paper which is disposed over the absorbent layer 30 so as completely to cover the narrow waist thereof whilst extending completely along its length, thus forming a composite layer. FIG. 2c shows an innermost layer 32 formed of 100% thermo-bonded polypropylene which is disposed over the second layer 31, whilst FIG. 2d shows an outermost layer 33 formed of non-absorbent nylon and which is disposed over the absorbent layer 30 so that the absorbent layer/tissue composite is sandwiched between the innermost and outermost layers 32 and 33, respectively.

FIG. 3a shows a modified second layer 34 replacing the second layer 31 shown in FIG. 2b, whilst FIG. 3b shows a modified outermost layer 35 for replacing the outermost layer 33 shown in FIG. 2d. Thus, the second layer 34 now corresponds to the liner 10 described above with reference to FIG. 1 of the drawings. At opposite ends thereof are respective pairs of three connection points 36 and 37 each connected to a respective electrically conductive track and which must be aligned with corresponding apertures 38 and 39 formed at opposite ends of the outermost layer 35. When a diaper is formed by combining the absorbent layer 30 with the modified second layer 34 and is sandwiched between the innermost layer 32 and the modified outermost layer 35, an external moisture alarm circuit can be connected to an external surface of the diaper at either a front or rear surface thereof, by connecting the moisture alarm circuit to either set of connection points 36 or 37 through the corresponding apertures 38 or 39 in the outermost layer 35.

It will be appreciated that, if desired, the apertures 38 and 39 can be formed in the innermost layer 32, this being disposed over the liner 34 and the unmodified outermost layer 33 being disposed over the absorbent layer 30. In practice, the difference between the two arrangements is that if the apertures 38 and 39 are formed in the outermost layer, then the external moisture alarm circuit is connected to an external surface of the diaper whilst if the apertures 38 and 39 are formed in the innermost layer, then the moisture alarm circuit is connected to an internal surface of the diaper, i.e. between the diaper and the user. Such an arrangement results in the moisture alarm circuit being less obtrusive but obviously it must be rendered sufficiently miniature so as not to obstruct the wearer. Furthermore, such an arrangement dictates that the moisture alarm circuit be of the type which either gives an audible signal, since a visible signal will not be seen, or of the type that transmits a signal for remote detection by an receiver/indicator monitor.

FIG. 4a shows the essential features of a production line for manufacturing a disposable diaper. A preliminary stage 40 comprises a pair of rollers 41 and 42 which feed material 43 into a heat treatment plant 44 from which there emerges an absorbent pad 45 similar in texture to cotto-nwool. All the features of the preliminary stage 40 are completely standard in diaper production plants and so will not be described in further detail.

The absorbent pad, or layer, 45 progresses along a conveyor belt 46 and is cut by a cutter 47 so as to have a generally I-shaped contour as shown in FIG. 4b and as shown in elevation in FIG. 4c.

Downstream of the preliminary stage 40 is a drum 48, constituting a first roll, which feeds a tissue-type material 49 under a guide rail 50 so that, as the absorbent layer 45 passes underneath the guide rail 50, the tissue-type layer 49 is compacted on to the absorbent layer 45 thus forming a composite layer which is cut by a cutter 51 so that the tissue-type layer 49 extends along the complete length of the absorbent layer 45 and across the narrow section of its I-shaped contour. The composite layer passes along the conveyor belt 46, downstream of which are disposed, on opposite sides of the conveyor belt 46, a pair of drums 52 and 53 constituting, respectively, second and third rolls, which feed corresponding innermost and outermost layer material 54 and 55 so as to cover opposite surfaces of the composite layer comprising the absorbent layer 45 and the tissue-type layer 49. The resulting assembly is cut by a cutter 56 so as to produce the finished diaper shown in plan in FIG. 4f and in elevation in FIG. 4g.

It will be understood that FIG. 4a shows only the principal stages of the diaper-manufacturing process. In practice, additional rolls of material may be provided for adding decorative liners to an external surface of the diaper and for providing the elasticated gusset which ensures a tight fit between the diaper and the groin area, and also for providing the sticky tabs by means of which the diaper is secured in use. However, these are not essential components of the invention and so are not described in detail.

It is a feature of the production line shown schematically in FIG. 4a that the first roll 48 bearing the tissue-type material 49 can be stopped, as required, in order to effect correct alignment with the absorbent layer 45. In practical prior art systems, the only alignment which needs to be effected is in order to ensure that a free end of each of the rolls of material 49, 54 and 55 overhangs the absorbent layer 45 or the absorbent layer/tissue composite, as appropriate, whereupon the speeds of the rolls 48, 52 and 53 are synchronized with the speed of the conveyor belt 46 so as to ensure that all subsequent layers of each successive diaper are correctly aligned.

In order to employ such a production line for manufacturing diapers in accordance with the invention, all that needs to be done is to take the first roll 48 of tissue-type material 49 and pre-print thereon, at regularly spaced and known intervals, the electrically conductive tracks shown in FIG. 1 of the drawings. The conductive tracks can be printed, for example, using a conductive ink such as sold by Coates Lorilleux under the trade names Silver 26-8204 and Graphite 26-8203. The pre-printed roll 48 is replaced in the production line and is synchronized such that, at the start of the process, the liner which now constitutes the tissue-type material 49 is correctly positioned on the absorbent layer 45 so that the two sets of connection terminals 36 and 37 (shown in FIG. 3a) are correctly located at opposite ends of the absorbent layer 45. Additionally, between the cutter 56 and the second roll 52, there is disposed a hole-cutter 57 which forms the apertures 38 and 39 (see FIG. 3b) in the outermost layer material 54. The speed of the roll 52 is synchronized with the vertical displacement of the hole-cutter 57 so that the resulting apertures 38 and 39 are correctly spaced and the speed of the roll 52 further being synchronized with the horizontal motion of the conveyor belt 46 so that the outermost layer 54 overlays the absorbent layer/liner composite with the apertures 38 and 39 correctly aligned with the sets of connection terminals 36 and 37.

It should be noted that the required synchronization is, in any event, a conventional feature of diaper production lines and there is therefore no need to elaborate further as to how the synchronization is effected.

It will readily be appreciated that, if desired, the rolls 52 and 53 can be reversed so that the innermost layer material 55 covers the liner 49, with the apertures 38 and 39 being formed in the innermost layer material 55. Alternatively, there may be provided two liners: an upper non-conductive liner and a lower liner of similar material but having printed thereon the conductive tracks. In this case, of course, the hole-cutter 57 must be located underneath the conveyor belt 46 so as to cut apertures in the innermost layer 55 proximate the pre-printed liner. Furthermore, if it be required to allow connection of an external moisture alarm circuit to both the internal and external surfaces of the diaper, then corresponding apertures can be formed in both the outermost layer 54 and the innermost layer 55 so that all options are covered.

Figure 5:
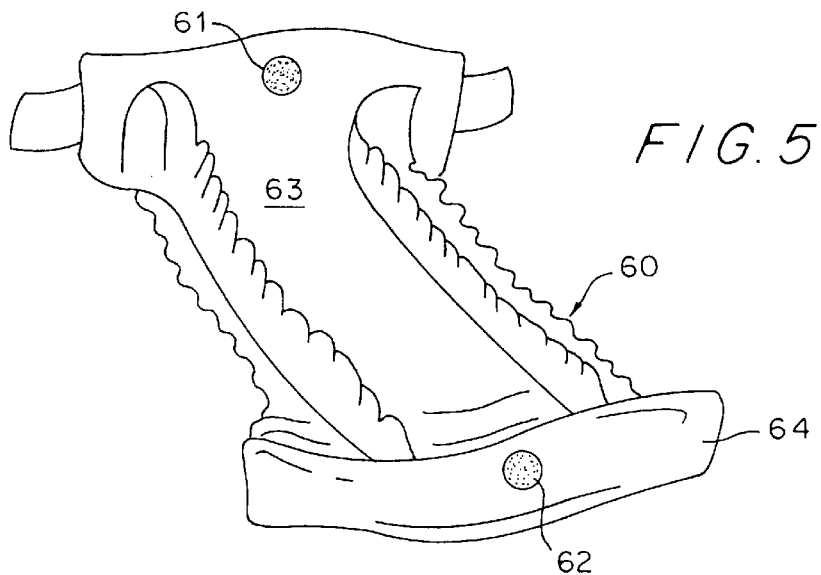
FIG. 5 is a pictorial representation of a diaper according to the invention.

FIG. 5 is a pictorial representation of a diaper 60 according to the invention in which apertures 61 and 62 are formed on an internal surface 63 and an external surface 64 of the diaper 60 in the manner just described. In order to facilitate connection of an external moisture alarm circuit to the three connection pads within the respective apertures 61 and 62, the connection pads are covered with respective layers of double-sided conductive adhesive transfer tape such as that manufactured by the 3M Company under the brand name Scotch 9703. Such tape comes with a releasable liner which can be peeled off prior to use, whereupon the corresponding connection points of the moisture alarm circuit can easily be connected to the connection terminals of the liner.

Figure 6:
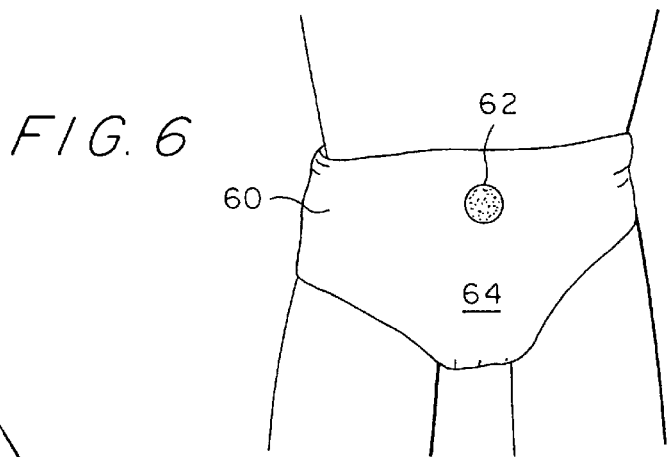
FIG. 6 is a pictorial representation of the diaper shown in FIG. 5 when in use.

FIG. 6 is a pictorial representation of the diaper 60 in use and further showing the aperture 62 formed in the external surface 64 of the diaper 60.

Figure 7A:
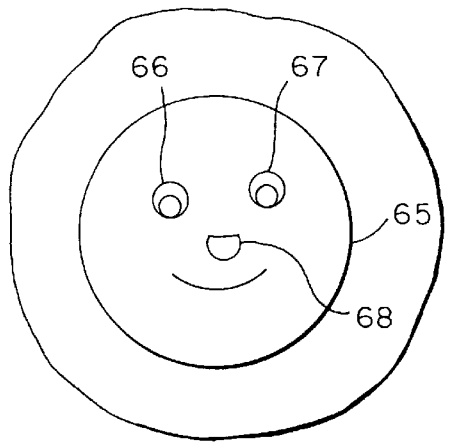
FIGS. 7a and 7b are pictorial and schematic representations, respectively, of a detail of a moisture alarm unit for coupling to the diaper shown in FIGS. 5 and 6.
Figure 7B:
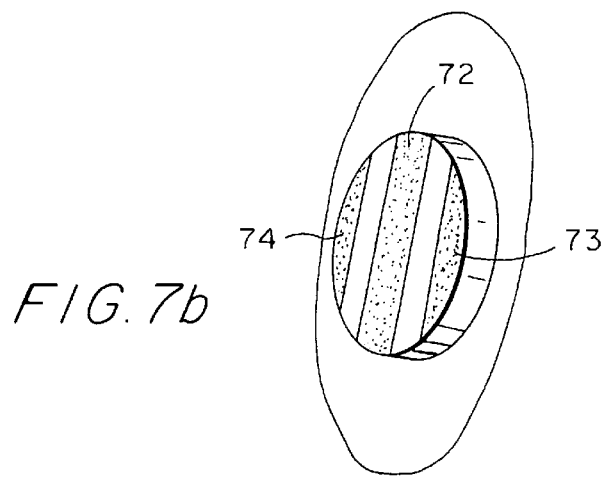

FIGS. 7a and 7b relate to a detail of a moisture alarm circuit having a casing shown generally as 65 and having on an upper surface thereof the general features of a face having eyes 66 and 67 and a nose 68 so as to render the resulting moisture alarm circuit attractive, particularly to young children. The eyes 66 and 67 and the nose 68 are connected to respective electrically conductive tracks 72, 73 and 74 on a rear surface of the casing as shown in FIG. 7b so that, when the moisture alarm unit is positioned upright on the connection pads 21, 22 and 23 or 21', 22' and 23', the latter will make correct contact with the electrically conductive tracks 72, 73 and 74 on the rear surface of the casing. This provides an easy way of ensuring correct orientation of the moisture alarm circuit.

Figure 8A:
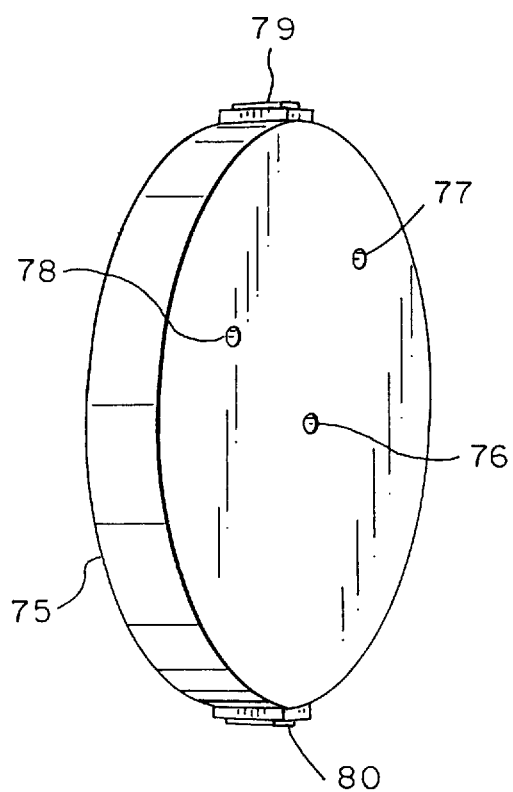
FIGS. 8a and 8b are pictorial representations of a detail of the moisture alarm unit shown in FIGS. 7a and 7b showing their connection to a diaper.

FIG. 8a shows pictorially a moisture alarm module shown generally as 75 in which are formed three sockets 76, 77 and 78 each for connecting to a respective conductive track on the diaper liner. A pair of diametrically placed resilient clasps 79 and 80 allow for a spring loaded retaining member (not shown) to be releasably disposed in a region of each socket so as to maintain frictional contact with a pin inserted therein and thus prevent its accidental removal.

Figure 8B:
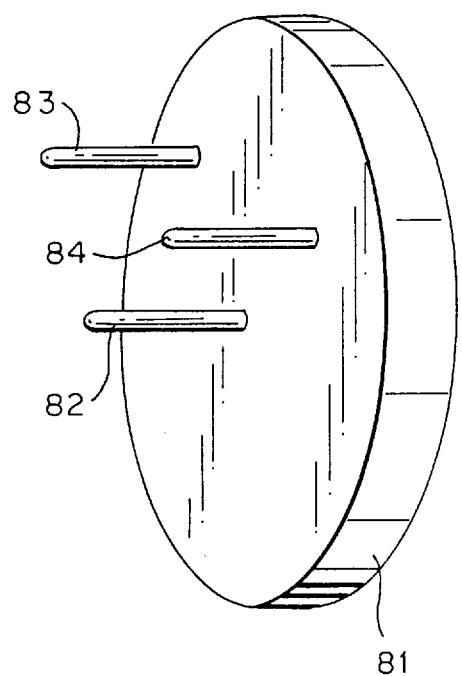

FIG. 8b shows pictorially a corresponding base member 81 formed of plastics having three protruding electrically conductive pins, 82, 83 and 84 each for aligning with a corresponding aperture in the diaper liner so as to protrude outwards therefrom and effect electrical contact with a corresponding one of the conductive tracks of the liner. The alarm module 75 is then attached to the base member 81 by applying pressure to the clasps 79 and 80 whereupon each of the protruding pins 82, 83 and 84 may be inserted into the corresponding socket 76, 77 and 80. By such means, each of the sockets 76, 77 and 78 may be electrically connected to a corresponding one of the conductive tracks of the liner. The pins 82, 83 and 84 may be formed of an electrically conductive material, such as metal, or may be formed by plating a plastic pin with an electrically conductive layer. The base member 81 may, if desired, be placed adjacent the user's skin so that the pins protrude through the diaper or, alternatively, a pocket may be formed in the diaper at an end thereof for accommodating therein the base member 81 so that it make no physical contact with the user.

The invention also encompasses within its scope the use of a moisture alarm circuit having two channels respectively connected to the terminals 21 and 22, on the one hand and 21 and 23 on the other hand, or, to the complementary pairs of terminals 21', 22' and 21', 23'. Each channel of the moisture alarm circuit is adapted to provide a different signal, permitting immediate discrimination to be effected as to which region of the liner within the diaper is soiled. For example, different colored indication lamps might be provided; or, alternatively, different frequency audio signals. Likewise, if the moisture alarm circuit is of the type having a transmitter connected to the diaper for communicating with a remote receiver/indicator, then different frequency signals can be transmitted from each of the two channels. Moisture alarm circuits per se are well described in U.S. Pat. No. 5,036,859 and it is well within the scope of one of average skill in the art to adapt such circuits to the specific requirements of the present invention.

It will be appreciated that whilst the liner is particularly suitable for integration in a disposable diaper during manufacture thereof, it can also be sold as a separate entity so as to be manually fitted within a disposable diaper in much the same way that prior art disposable pads are employed. The particular novelty of such liners resides primarily in the ease with which an external moisture alarm circuit can be connected thereto, and further in the provision thereon of two distinct regions which are separately monitored by respective conductive tracks.

Although, in the preferred embodiment, the diaper is constructed with adhesive contacts for connecting the moisture alarm circuit thereto, it will be appreciated that other forms of connection may be employed and fall within the scope of the invention. It will be understood, that instead of providing the double-sided adhesive tape integral with the alarm circuit, it may instead be an integral part of the outer lining of the diaper. In this case, the conducting pins of the diaper liner may be brought out to contacts on an upper surface of the adhesive tape whose lower adhesive surface is stuck on to the outer lining of the diaper. The upper surface of the adhesive tape is covered with a releasable liner which is peeled off prior to use, whereupon the corresponding connection points of the moisture alarm circuit can easily be connected to the connection terminals of the liner by locating on the now exposed adhesive upper surface of the adhesive tape.

I claim:

1. A liner for a diaper, said liner comprising:
    an electrically insulating sheet material having disposed thereon first, second and third separated electrically conductive tracks which become short-circuited when the liner is exposed to moisture, at least one end of each of the electrically conductive tracks being in the form of a conductive pad printed on the liner for permitting easy connection thereto of a moisture alarm circuit; wherein:
    the first electrically conductive track forms a common rail extending across an upper and lower portion of the liner, the second electrically conductive track extends across only the upper portion of the liner, and the third electrically conductive track is mutually separated from the first and second electrically conductive tracks and extends across only the lower portion of the liner;

so that, in use, the first and second electrically conductive tracks are short-circuited by urine and the first and third electrically conductive tracks are short-circuited by feces.

2. The liner according to claim 1, wherein:

the first track is in the form of a generally S-shaped rail extending longitudinally from a first end of the liner partially along a first side thereof and continuing partially along a second side of the liner towards a second end thereof, the second track extends longitudinally from the first end of the liner at least partially along the second side thereof, the third track extends longitudinally from the second end of the liner at least partially along the first side thereof, a first pair of equipotential bars interconnects the first and second tracks and extends laterally therebetween towards the first end of the liner so as to form a maze-shaped matrix which, in use, is disposed towards a front portion of the diaper, and a second pair of equipotential bars interconnects the first and third tracks and extends laterally therebetween towards the second end of the liner so as to form a maze-shaped matrix which, in use, is disposed towards a rear portion of the diaper.

3. The liner according to claim 1, being integral with a disposable diaper between first and second outer layers thereof, at least one of which has an aperture formed in at least one end thereof overlying respective ones of said conductive pads so as to facilitate proper connection to said conductive pads of a moisture alarm circuit.

4. The liner according to claim 3 being disposed behind an outermost layer of said diaper so as to permit connection of the moisture alarm circuit to said outermost layer.

5. The liner according to claim 4, wherein conductive pads are provided at opposite ends of said electrically conductive tracks and apertures are formed at opposite ends of the diaper so as to allow connection of a moisture alarm circuit to either a rear or front surface of the diaper.

6. The liner according to claim 3 being disposed behind an innermost layer of said diaper so as to permit connection of the moisture alarm circuit to said innermost layer.

7. The liner according to claim 3, further comprising a base member having protruding therefrom an electrically conductive pin in respect of each of said electrically conductive tracks for inserting through the corresponding aperture in the diaper so as to permit connection of the moisture alarm circuit thereto.

8. The liner according to claim 1, further comprising a removable seal adhered to the conductive pads which is peeled away before connecting the moisture alarm circuit.

9. A diaper including an absorbent layer between innermost and outermost layers and further including between the absorbent layer and one of said innermost or outermost layers the liner according to claim 3.

10. A moisture alarm circuit for use with a diaper having an absorbent layer between innermost and outermost layers and further including between the absorbent layer and one of the innermost or outermost layers the liner according to claim 1, said moisture alarm circuit comprising:

first and second independent moisture detector means for connecting, respectively, across the first and second and the first and third tracks of said liner so as to produce a respective indication signal when the first and second tracks are short-circuited or when the first and third tracks are short-circuited.

11. The alarm circuit according to claim 10, mounted in a casing having on an upper surface thereof the general features of a face having a pair of eyes and a nose, connected to respective electrically conductive tracks on a rear surface of the casing so that when the alarm circuit is mounted on to the diaper with the face correctly orientated, said electrically conductive tracks are located for maintaining electrical contact with the first, second and third tracks of the liner.

12. A liner for a diaper, said liner comprising:

an electrically insulating sheet material having disposed thereon first, second and third separated electrically conductive tracks which become short-circuited when the liner is exposed to moisture, at least one end of each of the electrically conductive tracks being in the form of a conductive pad printed on the liner for permitting easy connection thereto of a moisture alarm circuit; wherein:

first and second rails extend longitudinally from an end of the liner at least partially along a length thereof, two sets of equipotential bars are connected each to respective ones of said rails and extend laterally therebetween so as to form a maze-shaped matrix which, in use, is disposed towards a front portion of a diaper, the first electrically conductive track forms a common rail extending across an upper and lower portion of the liner, the second electrically conductive track extends across only the upper portion of the liner, and the third electrically conductive track is mutually separated from the first and second electrically conductive tracks and extends across only the lower portion of the liner;

so that, in use, the first and second electrically conductive tracks are short-circuited by urine and the first and third electrically conductive tracks are short-circuited by feces.

13. The liner according to claim 12, wherein the first, second and third tracks each extend from a first end of the liner to a second end thereof and are terminated at respective conductive pads.

* * * * *